(12) United States Patent
Anglada et al.

(10) Patent No.: US 8,158,632 B2
(45) Date of Patent: Apr. 17, 2012

(54) PYRAZOLO[1,5-A]PYRIMIDINES, PROCESSES, USES AND COMPOSITIONS

(75) Inventors: Luis Anglada, Barcelona (ES); Albert Palomer, Barcelona (ES); Antonio Guglietta, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 256 days.

(21) Appl. No.: 12/376,250

(22) PCT Filed: Aug. 2, 2007

(86) PCT No.: PCT/EP2007/058006
§ 371 (c)(1),
(2), (4) Date: Jun. 9, 2009

(87) PCT Pub. No.: WO2008/015253
PCT Pub. Date: Feb. 7, 2008

(65) Prior Publication Data
US 2009/0264448 A1    Oct. 22, 2009

Related U.S. Application Data

(60) Provisional application No. 60/835,444, filed on Aug. 4, 2006.

(30) Foreign Application Priority Data

Aug. 4, 2006 (EP) .................................... 06118454

(51) Int. Cl.
*A01N 43/90* (2006.01)
*A61K 31/519* (2006.01)
*C07D 487/00* (2006.01)

(52) U.S. Cl. ..................................... 514/259.3; 544/281
(58) Field of Classification Search ........................ None
See application file for complete search history.

(56) References Cited

U.S. PATENT DOCUMENTS

| 4,626,538 | A | | 12/1986 | Dusza et al. | |
|---|---|---|---|---|---|
| 4,847,256 | A | * | 7/1989 | Tseng et al. | ................ 514/259.3 |
| 6,399,621 | B1 | | 6/2002 | Dusza et al. | |

FOREIGN PATENT DOCUMENTS

| WO | WO-2005/014596 A1 | 2/2005 |
|---|---|---|
| WO | WO-2005/014597 A1 | 2/2005 |
| WO | WO 2006/136530 A1 | 12/2006 |
| WO | WO-2006/136560 A1 | 12/2006 |

OTHER PUBLICATIONS

Dorwald F. A. Side Reactions in Organic Synthesis, 2005, Wiley: VCH, Weinheim p. IX of Preface.*
Vippagunta et. al. Advanced Drug Delivery Reviews 48 (2001) 3-26.*
George, C.: "Pyrazolopyrimidines", The Lancet, vol. 358, pp. 1623-1626, (Nov. 10, 2001).

* cited by examiner

*Primary Examiner* — Jeffrey Murray
(74) *Attorney, Agent, or Firm* — Birch, Stewart, Kolasch & Birch, LLP

(57) ABSTRACT

The invention provides novel pyrazolo[1,5-a]pyrimidines which are useful for treating or preventing anxiety, epilepsy and sleep disorders including insomnia, and for inducing sedation-hypnosis, anesthesia, sleep and muscle relaxation.

11 Claims, No Drawings

PYRAZOLO[1,5-A]PYRIMIDINES, PROCESSES, USES AND COMPOSITIONS

This application is the National Phase of PCT/EP2007/058006 filed on Aug. 2, 2007, which claims priority under 35 U.S.C. 119(e) to U.S. Provisional Application No. 60/835,444 filed on Aug. 4, 2006 and under 35 U.S.C. 119(a) to Patent Application No. 06118454.5 filed in Europe on Aug. 4, 2006, all of which are hereby expressly incorporated by reference into the present application.

TECHNICAL FIELD

This invention is directed to agents with affinity for $GABA_A$ receptor, specifically to pyrazolo[1,5-a]pyrimidines, and more specifically to N-{2-substituted-5-[3-substituted-pyrazolo[1,5-a]pyrimidin-7-yl]-phenyl}-N-methyl-acetamides and N-{2-substituted-5-[3-substituted-pyrazolo[1,5-a]pyrimidin-7-yl]-phenyl}-N-methyl-methanesulfonamides.

BACKGROUND OF THE INVENTION $GABA_A$ receptor (γ-aminobutyric acid$_A$) is a pentameric protein which forms a membrane ion channel. $GABA_A$ receptor is implicated in the regulation of sedation, anxiety, muscle tone, epileptogenic activity and memory functions. These actions are due to defined subunits of $GABA_A$ receptor, particularly the $\alpha_1$- and $\alpha_2$-subunits.

Sedation is modulated by the $\alpha_1$-subunit. Zolpidem is characterized by a high affinity for the $\alpha_1$-receptors and its sedative and hypnotic action is mediated by these receptors in vivo. Similarly, the hypnotic action of zaleplon is also mediated by the $\alpha_1$-receptors.

The anxiolytic action of diazepam is mediated by the enhancement of GABAergic transmission in a population of neurons expressing the $\alpha_2$-receptors. This indicates that the $\alpha_2$-receptors are highly specific targets for the treatment of anxiety.

Muscle relaxation in diazepam is mainly mediated by $\alpha_2$-receptors, since these receptors exhibit a highly specific expression in spinal cord.

The anticonvulsant effect of diazepam is partly due to $\alpha_1$-receptors. In diazepam, a memory-impairing compound, anterograde amnesia is mediated by $\alpha_1$-receptors.

$GABA_A$ receptor and its $\alpha_1$- and $\alpha_2$-subunits have been widely reviewed by H. Möhler et al. (J. Pharmacol. Exp. Ther., 300, 2-8, 2002); H. Möhler et al. (Curr. Opin. Pharmacol., 1, 22-25, 2001); U. Rudolph et al. (Nature, 401, 796-800, 1999); and D. J. Nutt et al. (Br. J. Psychiatry, 179, 390-396, 2001).

Diazepam and other classical benzodiazepines are extensively used as anxiolytic agents, hypnotic agents, anticonvulsants and muscle relaxants. Their side effects include anterograde amnesia, decrease in motor activity and potentiation of ethanol effects.

In this context, the compounds of this invention are ligands of $\alpha_1$- and $\alpha_2$-$GABA_A$ receptor for their clinical application in sleep disorders, preferably insomnia, anxiety and epilepsy.

Insomnia is a highly prevalent disease. Its chronicity affects 10% of the population and 30% when transitory insomnia is computed as well. Insomnia describes the trouble in getting to sleep or staying asleep and is associated with next-day hangover effects such as weariness, lack of energy, low concentration and irritability. The social and health impact of this complaint is important and results in evident socioeconomic repercussions.

Pharmacological therapy in the management of insomnia firstly included barbiturates and chloral hydrate, but these drugs elicit numerous known adverse effects, for example, overdose toxicity, metabolic induction, and enhanced dependence and tolerance. In addition, they affect the architecture of sleep by decreasing above all the duration and the number of REM sleep stages. Later, benzodiazepines meant an important therapeutic advance because of their lower toxicity, but they still showed serious problems of dependence, muscle relaxation, amnesia and rebound insomnia following discontinuation of medication.

The latest known therapeutic approach has been the introduction of non-benzodiazepine hypnotics, such as pyrrolo[3,4-b]pyrazines (zopiclone), imidazo[1,2-a]pyridines (zolpidem) and, finally, pyrazolo[1,5-a]pyrimidines (zaleplon). Later, two new pyrazolo[1,5-a]pyrimidines, indiplon and ocinaplon, have entered into development, the latter with rather anxiolytic action. All these compounds show a rapid sleep induction and have less next-day hangover effects, lower potential for abuse and lower risk of rebound insomnia than benzodiazepines. The mechanism of action of these compounds is the allosteric activation of $GABA_A$ receptor through its binding to benzodiazepine binding site (C. F. P. George, The Lancet, 358, 1623-1626, 2001). While benzodiazepines are unspecific ligands at $GABA_A$ receptor binding site, zolpidem and zaleplon show a greater selectivity for $\alpha_1$-subunit. Notwithstanding that, these drugs still affect the architecture of sleep and may induce dependence in long-term treatments.

A variety of related pyrazolo[1,5-a]pyrimidines have been disclosed in patent publications U.S. Pat. Nos. 4,178,449, 4,281,000, 4,521,422 (2-pyridinyl[7-(4-pyridinyl)pyrazolo[1,5-a]pyrimidin-3-yl]methanone, ocinaplon), U.S. Pat. Nos. 4,576,943, 4,626,538 (N-{3-[3-(cyanopyrazolo[1,5-a]pyrimidin-7-yl]-phenyl}-N-ethyl-acetamide, zaleplon), U.S. Pat. Nos. 4,654,347, 6,399,621 (N-{3-[3-(thiophene-2-carbonyl)-pyrazolo[1,5-a]pyrimidin-7-yl]-phenyl}-N-methyl-acetamide, indiplon), WO2005014596, WO2005014597 and in WO 2006136530.

Research for new active compounds in the management of insomnia answers an underlying health need, because even recently introduced hypnotics still affect the architecture of sleep and may induce dependence in long-term treatments.

It is therefore desirable to focus on the development of new hypnotic agents with a lower risk of side effects.

SUMMARY OF THE INVENTION

Inventors have found new pyrazolo[1,5-a]pyrimidines which are active versus $GABA_A$ and, particularly, versus its $\alpha_1$- and $\alpha_2$-subunits. Consequently, the compounds of this invention are useful in the treatment and prevention of all those diseases mediated by $GABA_A$ receptor $\alpha_1$- and $\alpha_2$-subunits. Non-limitative examples of such diseases are sleep disorders, preferably insomnia, anxiety and epilepsy. Non-limitative examples of the relevant indications of the compounds of this invention are all those diseases or conditions, such as insomnia or anesthesia, in which an induction of sleep, an induction of sedation or an induction of muscle relaxation are needed.

Zaleplon, the pyrazolo[1,5-a]pyrimidine reference compound, is a structurally similar compound to the compounds of the present invention. However, zaleplon exhibits an extensive biotransformation due to aldehyde oxidase (B. G. Lake et al., Metabolism of zaleplon by human liver: evidence for involvement of aldehyde oxidase, Xenobiotica, 2002 October; 32(10):835-47; and K. Kawashima et al., Aldehyde oxidase-dependent marked species difference in hepatic metabolism of the sedative-hypnotic zaleplon, between monkeys and rats, Drug Metab Dispos. 1999 March; 27(3):422-8). Although another pyrazolo[1,5-a]pyrimidine with better metabolic stability than zaleplon is known in the art, indiplon, this compound has the drawback of having higher toxicological effects, as shown by cell viability experiments.

The susceptibility of compounds to biotransformation is related to their metabolic stability, i.e. to the half-life of the drug in the body and whether it forms metabolites. These are important parameters to assess the bioavailability, toxicity, and dosing potential for drug-drug interaction, which, in turn, are important parameters in determining their potential for human use. In this respect, compounds with maximum metabolic stability minimize the potential for drug-drug interactions and need less frequent dosing intervals.

The compounds of the present invention show unexpected fewer biotransformations, i.e. higher metabolic stability than other known related pyrazolo[1,5-a]pyrimidines, which improves the pharmacokinetic profile facilitating the maintenance of pharmacological effect and affords an unsuspected indication for maintaining a complete night's sleep. This property is related to the substitution on the phenyl ring, i.e., substituents $R_3$ and $R_4$. Particularly good are compounds bearing electron withdrawing substituents on the phenyl ring.

In addition, the compounds of the present invention, as illustrated in the examples, also show a good in vivo sedation/hypnotic therapeutic activity and low toxicological effects as demonstrated in cell viability experiments.

Thus, the present invention relates to a compound of formula (I):

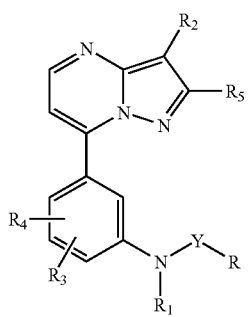

(I)

and pharmaceutically acceptable salts and hydrates thereof, which are ligands of $GABA_A$ receptor wherein R and $R_1$ represent alkyl($C_1$-$C_6$), $R_2$ is selected from the group consisting of cyano, nitro and thiophene-2-carbonyl, $R_3$ is selected from the group consisting of hydrogen and halogen, $R_4$ is selected from the group consisting of hydrogen, halogen, alkyl($C_1$-$C_6$) and alkoxy($C_1$-$C_6$), $R_5$ is selected from the group consisting of hydrogen and alkyl($C_1$-$C_6$), and Y is selected from the group consisting of —CO— and —$SO_2$—; and pharmaceutically acceptable salts and hydrates thereof.

It is another object of this invention to provide novel methods of treating or preventing anxiety, epilepsy and sleep disorders including insomnia, and for inducing sedation-hypnosis, anesthesia, sleep and muscle relaxation by administering a therapeutically effective amount of said compounds or a pharmaceutically acceptable salt or hydrate thereof.

DETAILED DESCRIPTION OF THE INVENTION

As it is said above, the present invention relates to a compound of formula (I):

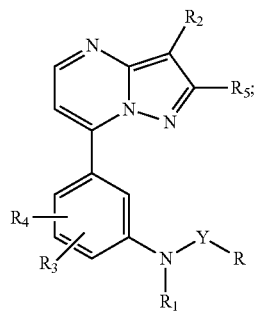

(I)

and pharmaceutically acceptable salts and hydrates thereof, wherein R, $R_1$, $R_2$, $R_3$, $R_4$, $R_5$ and Y are as mentioned above.

The term "pharmaceutically acceptable salt" used herein encompasses any salt formed from organic and inorganic acids, such as hydrobromic, hydrochloric, phosphoric, nitric, sulfuric, acetic, adipic, aspartic, benzenesulfonic, benzoic, citric, ethanesulfonic, formic, fumaric, glutamic, lactic, maleic, malic, malonic, mandelic, methanesulfonic, 1,5-naphthalendisulfonic, oxalic, pivalic, propionic, p-toluenesulfonic, succinic, tartaric acids and the like.

Specific compounds of formula (I) are selected from the group consisting of:

N-{2-fluoro-5-[3-nitro-pyrazolo[1,5-a]pyrimidin-7-yl]-phenyl}-N-methyl-acetamide;

N-{2-fluoro-5-[3-cyano-pyrazolo[1,5-a]pyrimidin-7-yl]-phenyl}-N-methyl-acetamide;

N-{2-chloro-5-[3-nitro-pyrazolo[1,5-a]pyrimidin-7-yl]-phenyl}-N-methyl-acetamide;

N-{2-chloro-5-[3-cyano-pyrazolo[1,5-a]pyrimidin-7-yl]-phenyl}-N-methyl-acetamide;

N-{2-fluoro-5-[3-nitro-pyrazolo[1,5-a]pyrimidin-7-yl]-phenyl}-N-methyl-methanesulfonamide;

N-{2-fluoro-5-[3-cyano-pyrazolo[1,5-a]pyrimidin-7-yl]-phenyl}-N-methyl-methanesulfonamide;

N-{2-chloro-5-[3-nitro-pyrazolo[1,5-a]pyrimidin-7-yl]-phenyl}-N-methyl-methanesulfonamide;

N-{2-chloro-5-[3-cyano-pyrazolo[1,5-a]pyrimidin-7-yl]-phenyl}-N-methyl-methanesulfonamide;

N-{2-fluoro-5-[3-cyano-2-methyl-pyrazolo[1,5-a]pyrimidin-7-yl]-phenyl}-N-methyl-acetamide;

N-{2-chloro-5-[3-cyano-2-methyl-pyrazolo[1,5-a]pyrimidin-7-yl]-phenyl}-N-methyl-acetamide;

N-{2-fluoro-5-[3-cyano-2-methyl-pyrazolo[1,5-a]pyrimidin-7-yl]-phenyl}-N-methyl-methanesulfonamide;

N-{2-chloro-5-[3-cyano-2-methyl-pyrazolo[1,5-a]pyrimidin-7-yl]-phenyl}-N-methyl-methanesulfonamide;

N-{2-methyl-5-[3-(thiophene-2-carbonyl)-pyrazolo[1,5-a]pyrimidin-7-yl]-phenyl}-N-methyl-acetamide;

N-{2-methoxy-5-[3-(thiophene-2-carbonyl)-pyrazolo[1,5-a]pyrimidin-7-yl]-phenyl}-N-methyl-acetamide;

N-{2,4-difluoro-5-[3-(thiophene-2-carbonyl)-pyrazolo[1,5-a]pyrimidin-7-yl]-phenyl}-N-methyl-acetamide; and N-{5-fluoro-2-methoxy-3-[3-(thiophene-2-carbonyl)-pyrazolo[1,5-a]pyrimidin-7-yl]-phenyl}-N-methyl-acetamide.

The following reaction Schemes illustrate the preparation of the compounds of the present invention.

Scheme 1

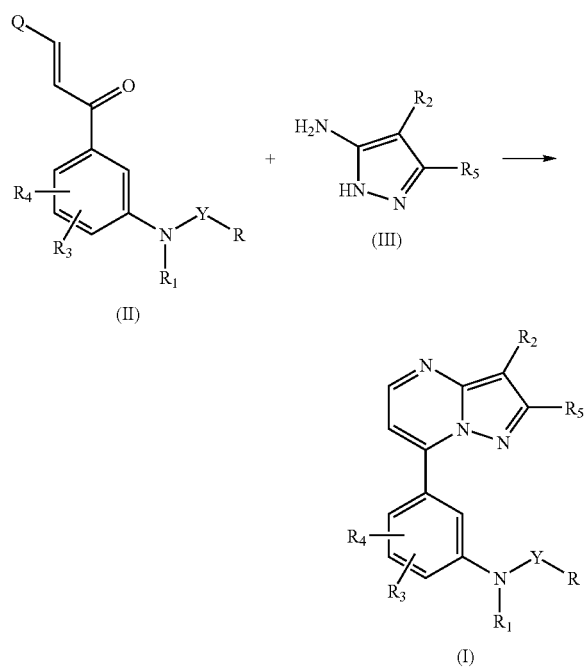

R, $R_1$, $R_2$, $R_3$, $R_4$, $R_5$ and Y are as described above, and Q is an appropriate leaving group selected from the group consisting of N(dialkyl($C_1$-$C_6$)), alkylthio($C_1$-$C_6$) and alkoxy($C_1$-$C_6$). Preferably Q is selected from the group consisting of dimethylamino, methylthio or methoxy.

The reaction of aminopyrazole of general formula (III) with an appropriately substituted 1-aryl-2-propen-1-one (II) is carried out in an inert polar protic or aprotic solvent such as glacial acetic acid, ethanol, methanol, dimethylformamide or dimethylsulfoxide at a temperature ranging from 50° to 130° C. After elapsing several hours (reaction time), the solvent is removed and the residue obtained is partitioned between an aqueous solution of sodium bicarbonate and dichloromethane. The crude resulting from evaporating the organic layer to dryness may be purified by one of the following methods: (a) silica gel chromatography using ethyl acetate or dichloromethane/methanol as eluent; or (b) crystallization in a suitable solvent (ethyl acetate, ethanol, methanol, etc.).

The intermediate of formula (II) when Q is dimethylamino [intermediate (VI)] can be obtained following the reaction sequence shown in Scheme 2

Scheme 2

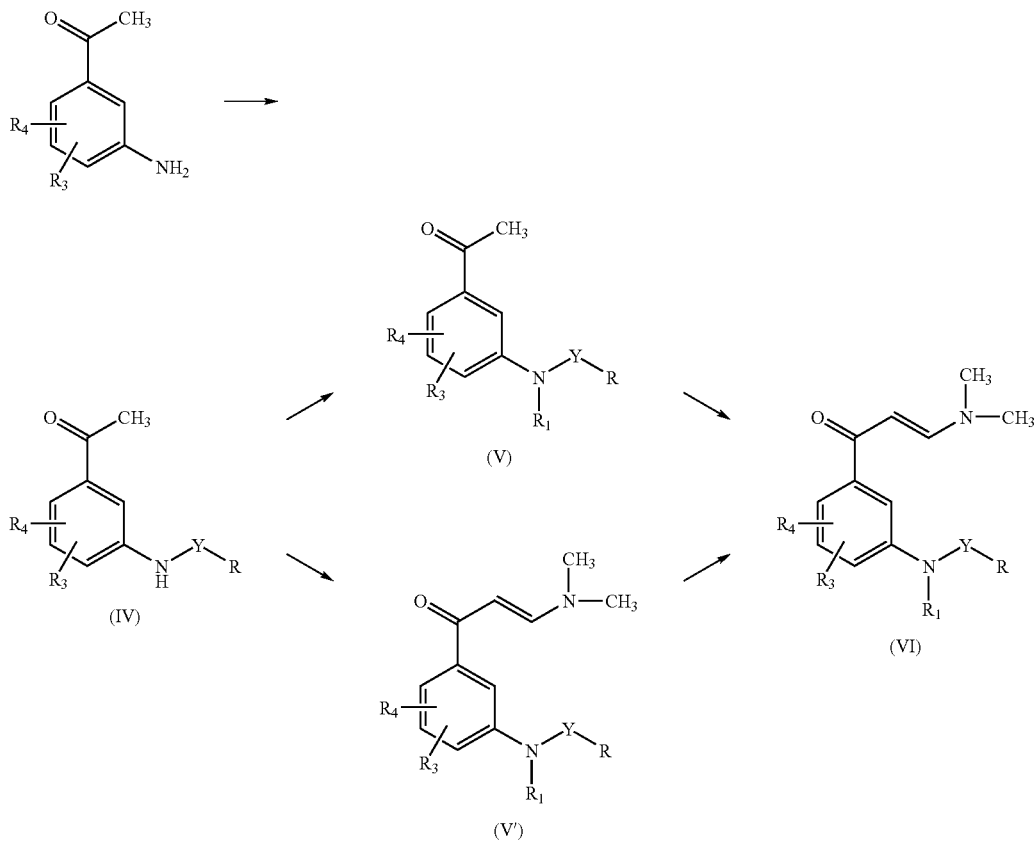

wherein R, $R_1$, $R_3$, $R_4$ and Y are as described above.

The intermediates of formula (IV) when Y is a sulfonyl group are prepared according to the method described by R. H. Uloth et al. (J. Med. Chem. 9, 88-96, 1966).

The alkylation of the intermediates (IV) leading to the intermediates of formula (V) is performed, in accordance with methods well known by experts in Organic Chemistry, via formation of an anion and subsequent reaction with an alkyl halide.

The enaminones of formula (V') and (VI) are prepared according to general synthetic procedures of enamines described by J. M. Domagala et al. (J. Heterocyclic Chem., 26(4), 1147-58, 1989); and K. Sawada et al. (Chem. Pharm. Bull., 49(7), 799-813, 2001) by reacting an acetophenone with N,N-dimethylformamide dimethylacetal (DMFDMA) or Bredereck's reagent (tert-butoxybis(dimethylamino) methane).

The intermediates of formula (II), when Q is dimethylamino, Y is sulfonyl and $R_1$ is methyl (VII), can alternatively be prepared according to Scheme 3

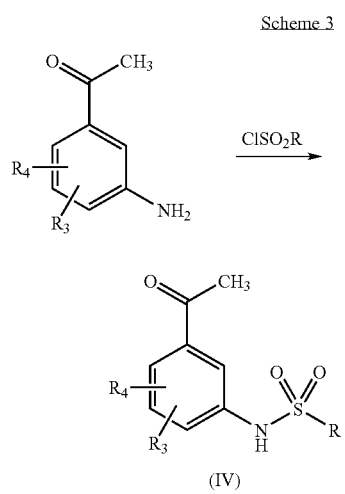

wherein R, $R_3$, and $R_4$ are as defined above.

The conversion of (IV) into (VII) leads to the formation of the enaminone and, simultaneously, the formation of the N-methyl-sulfonamide as a result of the use of the properties of the N,N-dimethylformamide dimethyl acetal as a methylating agent.

The intermediates of formula (II), when Q is dimethylamino, and $R_1$ is methyl (X), can also be prepared according to Scheme 4

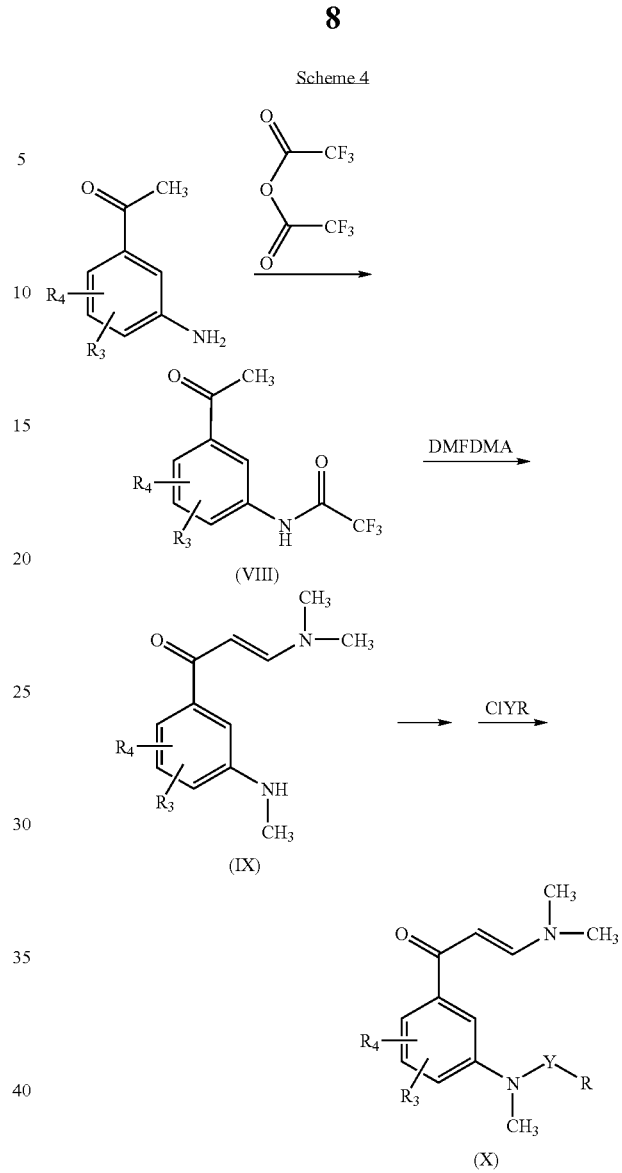

wherein R, $R_3$, $R_4$ and Y are as defined above.

The advantage of this process is based on the fact that the formation of the sulfonamide or carboxamide takes place in the last state of process. As a result, the total number of reaction steps is reduced in the preparation of large series of products. Moreover, as shown in the scheme, the conversion of (VIII) into (IX) leads to three following reactions in a one-pot process: (a) formation of the enaminone; (b) methylation of the trifluoroacetamide; and (c) deacylation yielding the N-methylated amine. The subsequent reaction of (IX) with the corresponding sulfonic acid chloride or carboxylic acid chloride leads to obtaining intermediates (X).

The compounds of the present invention or their pharmaceutically acceptable salts or hydrates can be used for the preparation of a medicament for treating or preventing diseases associated with $GABA_A$ receptor modulation in a human or non-human mammal. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

Another embodiment of the present invention is to provide the use of a compound of the present invention or a pharmaceutically acceptable salt or hydrate thereof for the preparation of a medicament for treating or preventing anxiety in a human or non-human mammal.

Another embodiment of the present invention is to provide the use of a compound of the present invention or a pharmaceutically acceptable salt or hydrate thereof for the preparation of a medicament for treating or preventing epilepsy in a human or non-human mammal in need thereof.

Another embodiment of the present invention is to provide the use of a compound of the present invention or a pharmaceutically acceptable salt or hydrate thereof for the preparation of a medicament for treating or preventing sleep disorders in a human or non-human mammal in need thereof.

Another embodiment of the present invention is to provide the use of a compound of the present invention or a pharmaceutically acceptable salt or hydrate thereof for the preparation of a medicament for treating or preventing insomnia in a human or non-human mammal in need thereof.

Another embodiment of the present invention is to provide the use of a compound of the present invention or a pharmaceutically acceptable salt or hydrate thereof for the preparation of a medicament for inducing sedation-hypnosis in a human or non-human mammal in need thereof.

Another embodiment of the present invention is to provide the use of a compound of the present invention or a pharmaceutically acceptable salt or hydrate thereof for the preparation of a medicament for inducing anesthesia in a human or non-human mammal in need thereof.

Another embodiment of the present invention is to provide the use of a compound of the present invention or a pharmaceutically acceptable salt or hydrate thereof for the preparation of a medicament for modulating the necessary time to induce sleep and its duration in a human or non-human mammal in need thereof.

Another embodiment of the present invention is to provide the use of a compound of the present invention or a pharmaceutically acceptable salt or hydrate thereof for the preparation of a medicament for inducing muscle relaxation in a human or non-human mammal in need thereof.

The present invention also relates to a method of treatment or prevention of a human or non-human mammal suffering from diseases associated with $GABA_A$ receptor modulation in a human or non-human mammal, which comprises administering to said human or non-human mammal in need thereof a therapeutically effective amount of a compound of the present invention or pharmaceutically acceptable salts or hydrates thereof, together with pharmaceutically acceptable diluents or carriers. More specifically, diseases associated with $GABA_A$ receptor modulation comprise diseases associated with $\alpha_1$-$GABA_A$ receptor modulation and/or $\alpha_2$-$GABA_A$ receptor modulation. A non-limitative list of such diseases comprises anxiety, epilepsy, sleep disorders, including insomnia, and the like.

As used herein, the term "mammal" shall refer to the Mammalian class of higher vertebrates. The term "mammal" includes, but is not limited to, a human.

Another embodiment of the present invention is to provide a pharmaceutical composition containing a compound of the present invention or pharmaceutically acceptable salts and hydrates thereof, in association with therapeutically inert carriers.

The compositions include those suitable for oral, rectal and parenteral (including subcutaneous, intramuscular, and intravenous) administration, although the most suitable route will depend on the nature and severity of the condition being treated. The most preferred route of the present invention is the oral route. The compositions may be conveniently presented in unit dosage form, and prepared by any of the methods well known in the art of pharmacy.

The active compound can be combined with a pharmaceutical carrier according to conventional pharmaceutical compounding techniques. The carrier may take a wide variety of forms depending on the form of the preparation desired for administration, e.g. oral or parenteral (including intravenous injections or infusions). In preparing the compositions for oral dosage form any of the usual pharmaceutical media may be employed. Usual pharmaceutical media include, for example, water, glycols, oils, alcohols, flavoring agents, preservatives, coloring agents, and the like, in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets) with the oral solid preparations being preferred over the oral liquid preparations.

Because of their ease of administration, tablets and capsules represent the most advantageous oral dosage unit form, in which case solid pharmaceutical carriers are employed. If desired, tablets may be coated by standard aqueous or non-aqueous techniques.

A suitable dosage range for use is from about 0.01 mg to about 100.00 mg total daily dose, given as a once daily administration or in divided doses if required.

The compounds of the present invention have a high affinity for $\alpha_1$- and $\alpha_2$-$GABA_A$ receptors. These in vitro results are consistent with those in vivo results obtained in sedation-hypnosis tests.

The pharmacological activity of the compounds of the present invention has been determined as shown below.

a) Ligand-Binding Assays. Determination of the Affinity of Test Compounds for $\alpha_1$- and $\alpha_2$-$GABA_A$ Receptor Male Sprague-Dawley rats weighing 200-250 g at the time of experiment were used. After decapitation of the animal, the cerebellum (tissue that mostly contains $\alpha_1$-$GABA_A$ receptor) and spinal cord (tissue that mostly contains $\alpha_2$-$GABA_A$ receptor) were removed. The membranes were prepared according to the method by J. Lameh et al. (Prog. Neuro-Psychopharmacol. Biol. Psychiatry, 24, 979-991, 2000) and H. Noguchi et al. (Eur. J. Pharm., 434, 21-28, 2002) with slight modifications. Once the tissues weighed, they were suspended in 50 mM Tris.HCl (pH 7.4), 1:40 (v/v), or sucrose 0.32 M in the case of spinal cord, homogenized and then centrifuged at 20000 g for 10 min at 7° C. The resulting pellet was resuspended under the same conditions and centrifuged again. The pellet was finally resuspended on a minimum volume and kept at −80° C. overnight. On the next day, the process was repeated until the final pellet was resuspended at a ratio of 1:10 (v/v) in the case of cerebellum and at a ratio of 1:5 (v/v) in the case of spinal cord.

Affinity was determined by competitive tests using radiolabeled flumazenil as ligand. The tests were performed according to the methods described by S. Arbilla et al. (Eur. J. Pharmacol., 130, 257-263, 1986); and Y. Wu et al. (Eur. J. Pharmacol., 278,125-132, 1995) using 96-well microtiter plates. The membranes containing the study receptors, flumazenil (radiolabeling at a final concentration of 1 nM) and ascending concentrations of test compounds (in a total volume of 230 μL in 50 mM [ph 7.4] Tris.HCl buffer) were incubated. Simultaneously, the membranes were only incubated with the radiolabeled flumazenil (total binding, 100%) and in the presence of an elevated concentration of unradiolabeled flumazenil (non-specific binding, % estimation of radiolabeled ligand). The reactions started on adding the radiolabeled ligand followed by incubation for 60 minutes at 4° C. At the end of the incubation period, 200 µL of reaction were transferred to a multiscreen plate (Millipore) and filtered using a vacuum manifold and then washed three times with cold test buffer. The multiscreen plates were equipped with a GF/B filter that retained the membranes containing the receptors and the radiolabeled ligand which had been bound to the receptors. After washing, the plates were left till dry. Once dried, scintillation liquid was added and left under stirring overnight. The next day the plates were counted using a Perkin-Elmer Microbeta scintillation counter.

For analysis of the results the percentage of specific binding for every concentration of test compound was calculated as follows:

% specific binding=$(X-N/T-N) \times 100$ where,

X: amount of bound ligand for every concentration of compound.

T: total binding, maximum amount bound to the radiolabeled ligand.

N: non-specific binding, amount of radiolabeled ligand bound in a non-specific way irrespective of the receptor used.

Every concentration of compounds was tested in triplicate and their mean values were used to determine the experimental values of % specific binding versus the concentration of compound. Affinity data are expressed as % inhibition at $10^{-5M}$ and $10^{-7M}$ concentrations for $\alpha_1$ subunit and at 10-5M for $\alpha_2$ subunit. The results of these tests are given in Tables 1 and 2 respectively.

TABLE 1

Affinity for the $\alpha_1$ subunit of the GABA$_A$ receptor

| Compound | % inhib $10^{-5M}$ | % inhib $10^{-7M}$ |
|---|---|---|
| Preparative example 5 | 98.2 | 42.3 |
| Preparative example 6 | 98.1 | 36.4 |
| Preparative example 11 | 97.7 | 41.8 |
| Preparative example 13 | 98.7 | 39.8 |
| Preparative example 14 | 97.3 | 31.9 |
| Zaleplon | 97.2 | 26.1 |

TABLE 2

Affinity for the $\alpha_2$ subunit of the GABA$_A$ receptor

| Compound | % inhib $10^{-5M}$ |
|---|---|
| Preparative example 5 | 94.5 |
| Preparative example 6 | 87.5 |
| Preparative example 11 | 95.0 |
| Zaleplon | 77.4 | b) In Vivo Determination of Predictive Sedative-Hypnotic Action

The in vivo effects of these compounds were assessed by a predictive sedation-hypnosis test in mice (D. J. Sanger et al., Eur. J. Pharmacol., 313, 35-42, 1996; and G. Griebel et al., Psychopharmacology, 146, 205-213, 1999).

Groups of 5-8 male CD1 mice, weighing 22-26 g at the time of test, were used. The test compounds were administered in single equimolecular intraperitoneal doses, suspended in 0.25% agar with one drop of Tween 80 in a volume of 10 mL/kg. Two doses were tested in each route. Control animals received the vehicle alone. Using a Smart System (Panlab, S. L., Spain) the traveled distance in cm is recorded for each mouse at 5-min intervals during a period of 30 minutes after intraperitoneal (ip) dosing. The inhibition percentage of traveled distance of treated animals versus control animals (the first 5 min were discarded) and ED$_{50}$ values were calculated. The results of this test are given in Tables 3 and 4.

TABLE 3

Determination of in vivo sedative-hypnotic activity in mice

| Compound | % inhib motor activity 98 µmol/kg |
|---|---|
| Preparative example 5 | 89.0 |
| Preparative example 6 | 76.3 |
| Preparative example 11 | 83.8 |
| Preparative example 13 | 95.6 |
| Preparative example 14 | 89.6 |
| Zaleplon | 84.9 |

TABLE 4

Determination of the ED$_{50}$ values in inducing sedation in mice

| Compound | ED$_{50}$ (µmol/kg) |
|---|---|
| Preparative example 11 | 16.9 |
| Example 2 of WO 2005014596 | 30.1 |
| Example 18 of WO 2005014596 | 19.9 |

Compared with other representative pyrazolo[1,5-a]pyrimidines of the prior art, the compound of example 11 of the present invention displayed a clearly lower ED$_{50}$. This implies that the compound of example 11 is more potent in vivo since a lower dose is needed for inducing the therapeutic effect.

c) In Vitro Determination of Metabolic Stability in Human Hepatocytes Cytosolic Fraction Compounds were dissolved in dimethyl sulfoxide to achieve an initial concentration of 10 mM. This stock solution was then diluted with solvent and buffer to obtain final assay concentration of 5 µM. Compounds were tested at a single concentration of 5 µM in duplicate incubating with 1.0 mg/mL of pooled human cytosol (obtained from Xenotech plc) at 37° C. Metabolism was assessed in the presence or absence of cofactors and measured as loss of parent compound by LC/MS analysis at 0, 60 and 120-minutes time points. Percentages of remaining parent compounds were then calculated. Results are shown in Table 5. A generic LC method was used:

| Mobile phase: | A = 0.1% Formic acid in water | | |
|---|---|---|---|
| | B = 0.1% Formic acid in acetonitrile | | |
| HPLC Column: | Higgins Clipius C18 5 µm, | | |
| | 50 × 3 mm | | |
| Flow rate: | 2 ml · min$^{-1}$ | | |
| | Time | % A | % B |
| Gradient: | 0.00 | 95 | 5 |
| | 2.00 | 5 | 95 |
| | 2.50 | 5 | 95 |
| | 2.60 | 95 | 5 |
| | 3.00 | 95 | 5 |

TABLE 5

Metabolic stability in human hepatocytes cytosolic fraction

| Compound | % of Parent | |
|---|---|---|
| | 60 min | 120 min |
| Preparative example 6 | 86 | 81 |
| Preparative example 11 | 88 | 82 |
| Zaleplon | 79 | 68 |
| Example 18 of WO 2005014596 | 73 | 46 |

Surprisingly, the compounds of preparative examples 6 and 11 show a higher percentage (10-20%) of the remaining parent compound compared with zaleplon and the prior art compound of WO 2005014596, after incubation for a period of 60 and 120 min. On the other hand, zaleplon has a lower percentage of the remaining parent compound at any timepoint and a higher biotransformation from 60 to 120 min.

d) In Vitro Determination of Cell Toxicity in HepG2, CHO-K1 and HeLa Cells at 24 h HepG2 (human hepatocellular carcinoma cells) and CHO-K1 (Chinese hamster ovary cells) were both obtained from the American Type Culture Collection (ATCC). HepG2 were cultured in Minimum Essential Medium (MEM) containing Earl's salts solution with 1.87 mM Glutamax® and supplemented with 1 mM sodium pyruvate, 0.1 mM non-essential amino acids, 100000 U/L penicillin, 100000 µg/L streptomycin and 10% Foetal Bovine Serum. CHO-K1 were maintained in Ham's F-12 medium containing 1 mM Glutamax® and supplemented with 1 mM L-glutamine, 100000 U/L penicillin, 100000 µg/L streptomycin and 10% Foetal Bovine Serum. Promega CellTiter 96® Aqueous One Solution Cell Viability Assay, contains the tetrazolium salt (MTS) that dehydrogenase enzymes found in metabolically active cells turn into the aqueous soluble formazan product. The quantity of formazan product is proportional to the number of living cells in culture.

Compounds were dissolved in DMSO to achieve an initial concentration of 100 mM. Serial dilutions were made from this stock solution in DMSO to achieve a range of concentrations from 50 to 0.25 mM. The stock solution and serial dilutions were then diluted 1:100 with the respective cell culture medium. In the case of CHO-K1 cells, concentrations at 1000, 500, 250, 100, 50, 25, 10, 5 and 2.5 µM were prepared to assess $IC_{50}$, whereas in the case of HepG2 cells, final concentrations at 1000, 100, 10 and 1 µM final were assayed in order to calculate the percentage of cell. The final DMSO concentration in all wells was 1% v/v. Cell lines were both incubated with test compounds for 24 hours. Relative cell viability was determined spectro-photometrically at 490 nm following the addition of the MTS dye and further one-hour incubation. Tamoxifen was used as the positive control.

An analogous protocol was used to determine the cell toxicity in HeLa cells at 24 h. Results are shown in Table 6.

TABLE 6 cell toxicity in HepG2, CHO-K1 and HeLa cells at 24 h

| Compound | % of cell viability | | $IC_{50}$ |
|---|---|---|---|
| | HepG2 at 100 µM | HeLa at 100 µM | CHO |
| Preparative example 11 | 84.5% | 83.9% | 185.6 µM |
| Example 1 of US 6399621 (indiplon) | 70% | 67.9% | 108.4 µM |

These results show that compound of example 11 of the present invention is less toxic than the reference compound indiplon, since the cell survival for compound of example 11 is higher than indiplon (84.5% vs. 70%) in the HepG2 cell line. These results were also confirmed in the other two cell lines assayed.

PREPARATIVE EXAMPLE 1

N-{2-fluoro-5-[3-nitro-pyrazolo[1,5-a]pyrimidin-7-yl]-phenyl}-N-methyl-acetamide

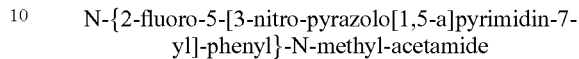

A mixture of 0.048 g (0.38 mmol) of 4-nitro-2H-pyrazol-3-ylamine and 0.1 g (0.38 mmol) of N-[5-(3-dimethylamino-acryloyl)-2-fluoro-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which was chromatographed (silica gel) using ethyl acetate-dichloromethane as eluent, thus affording 61 mg (yield 49%) of a solid corresponding to N-{2-fluoro-5-[3-nitro-pyrazolo[1,5-a]pyrimidin-7-yl]-phenyl}-N-methyl-acetamide.

$^1$H NMR (400 MHz, CDCl$_3$): δ 1.97 (3H, s), 3.29 (3H, s), 7.29 (1H, d, J=4.4 Hz), 7.45 (1H, t, J=8.4 Hz), 7.89-8.02 (1H, m), 8.07-8.09 (1H, m), 8.83 (1H, s), 9.0 (1H, d, J=4.4 Hz).

MS (ES) m/z=330 (MH$^+$)

HPLC=95.7%

PREPARATIVE EXAMPLE 2

N-{2-fluoro-5-[3-cyano-pyrazolo[1,5-a]pyrimidin-7-yl]-phenyl}-N-methyl-acetamide

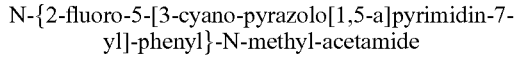

A mixture of 0.041 g (0.38 mmol) of 5-amino-1H-pyrazole-4-carbonitrile and 0.1 g (0.38 mmol) of N-[5-(3-dimethylamino-acryloyl)-2-fluoro-phenyl]-N-methyl-acetamide in 10 mL of glacial acetic acid was refluxed for 2.5 hours and then the solvent was removed by reduced pressure distillation. Dichloromethane (15 mL) and a saturated sodium bicarbonate solution (10 mL) were added to the resulting residue. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 95 mg of N-{2-fluoro-5-[3-cyano-pyrazolo[1,5-a]pyrimidin-7-yl]-phenyl}-N-methyl-acetamide as a solid (yield 81%).

$^1$H NMR (400 MHz, CDCl$_3$): δ 1.96 (3H, s), 3.28 (3H, s), 7.18 (1H, d, J=4.4 Hz), 7.42 (1H, t, J=8.8 Hz), 7.99-8.02 (1H, m), 8.09-8.12 (1H, m), 8.42 (1H, s), 8.79 (1H, d, J=4.4 Hz).

MS (ES) m/z=310 (MH$^+$)

HPLC=97.8%

PREPARATIVE EXAMPLE 3

N-{2-chloro-5-[3-nitro-pyrazolo[1,5-a]pyrimidin-7-yl]-phenyl}-N-methyl-acetamide

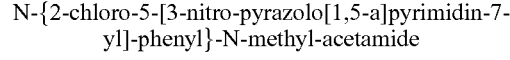

A mixture of 0.054 g (0.43 mmol) of 4-nitro-2H-pyrazol-3-ylamine and 0.120 g (0.43 mmol) of N-[5-(3-dimethylamino-acryloyl)-2-chloro-phenyl]-N-methyl-acetamide in 10 mL of glacial acetic acid was refluxed for 2.5 hours and then the solvent was removed by reduced pressure distillation. Dichloromethane (15 mL) and a saturated sodium bicarbonate solution (10 mL) were added to the resulting residue. The two layers were separated, and the aqueous layer was washed with 10 mL of dichloromethane. The organic layers were washed with 10 mL of water and dried over magnesium sulfate. The dichloromethane layer was evaporated to dryness to yield an oil which was chromatographed (silica gel) using ethyl acetate-dichloromethane as eluent, thus affording 35 mg (yield 24%) of a solid corresponding to N-{2-chloro-5-[3-nitro-pyrazolo[1,5-a]pyrimidin-7-yl]-phenyl}-N-methyl-acetamide.

$^1$H NMR (400 MHz, CDCl$_3$): δ 1.90 (3H, s), 3.26 (3H, s), 7.30 (1H, d, J=4.4 Hz), 7.77 (1H, d, J=8 Hz), 7.93 (1H, dd, J=2.4 and 8.4 Hz), 8.08 (1H, d, J=2 Hz), 8.83 (1H, s), 9.01 (1H, d, J=4.8 Hz).

MS (ES) m/z=346 (MH$^+$)
HPLC=91%

PREPARATIVE EXAMPLE 4

N-{2-chloro-5-[3-cyano-pyrazolo[1,5-a]pyrimidin-7-yl]-phenyl}-N-methyl-acetamide A mixture of 0.046 g (0.43 mmol) of 5-amino-1H-pyrazole-4-carbonitrile and 0.120 g (0.43 mmol) of N-[5-(3-dimethylamino-acryloyl)-2-chloro-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 108 mg of N-{2-chloro-5-[3-cyano-pyrazolo[1,5-a]pyrimidin-7-yl]-phenyl}-N-methyl-acetamide as a solid (yield 77%).

$^1$H NMR (400 MHz, CDCl$_3$): δ 1.90 (3H, s), 3.25 (3H, s), 7.20 (1H, d, J=4.4 Hz), 7.74 (1H, d, J=8.8 Hz), 7.94 (1H, dd, J=2.4 and 8.4 Hz), 8.10 (1H, d, J=2 Hz), 8.43 (1H, s), 8.80 (1H, d, J=4.8 Hz).

MS (ES) m/z=326 (MH$^+$)
HPLC=97.7%

PREPARATIVE EXAMPLE 5

N-{2-fluoro-5-[3-nitro-pyrazolo[1,5-a]pyrimidin-7-yl]-phenyl}-N-methyl-methanesulfonamide A mixture of 0.043 g (0.33 mmol) of 4-nitro-2H-pyrazol-3-ylamine and 0.1 g (0.33 mmol) of N-[5-(3-dimethylamino-acryloyl)-2-fluoro-phenyl]-N-methyl-methanesulfonamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which was chromatographed (silica gel) using ethyl acetate-dichloromethane as eluent, thus affording 58 mg (yield 48%) of a solid corresponding to N-{2-fluoro-5-[3-nitro-pyrazolo[1,5-a]pyrimidin-7-yl]-phenyl}-N-methyl-methanesulfonamide.

$^1$H NMR (400 MHz, CDCl$_3$): δ 3.02 (3H, s), 3.39 (3H, s), 7.29 (1H, d, J=4.4 Hz), 7.38-7.42 (1H, m), 8.05-8.13 (2H, m), 8.83 (1H, s), 8.98 (1H, d, J=4.4 Hz).

MS (ES) m/z=366 (MH$^+$)
HPLC=97.6%

PREPARATIVE EXAMPLE 6

N-{2-fluoro-5-[3-cyano-pyrazolo[1,5-a]pyrimidin-7-yl]-phenyl}-N-methyl-methanesulfonamide A mixture of 0.036 g (0.33 mmol) of 5-amino-1H-pyrazole-4-carbonitrile and 0.1 g (0.33 mmol) of N-[5-(3-dimethylamino-acryloyl)-2-fluoro-phenyl]-N-methyl-methanesulfonamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 81 mg of N-{2-fluoro-5-[3-cyano-pyrazolo[1,5-a]pyrimidin-7-yl]-phenyl}-N-methyl-methanesulfonamide as a solid (yield 70%).

$^1$H NMR (400 MHz, CDCl$_3$): δ 3.01 (3H, s), 3.38 (3H, s), 7.29 (1H, d, J=4.4 Hz), 7.36-7.41 (1H, m), 8.08-8.15 (2H, m), 8.42 (1H, s), 8.77 (1H, d, J=4.4 Hz).

MS (ES) m/z=346 (MH$^+$)
HPLC=99.1%

PREPARATIVE EXAMPLE 7

N-{2-chloro-5-[3-nitro-pyrazolo[1,5-a]pyrimidin-7-yl]-phenyl}-N-methyl-methanesulfonamide A mixture of 0.050 g (0.39 mmol) of 4-nitro-2H-pyrazol-3-ylamine and 0.124 g (0.39 mmol) of N-[5-(3-dimethylamino-acryloyl)-2-chloro-phenyl]-N-methyl-methanesulfonamide in 12 mL of glacial acetic acid was refluxed for 1.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 56 mg of N-{2-chloro-5-[3-nitro-pyrazolo[1,5-a]pyrimidin-7-yl]-phenyl}-N-methyl-methanesulfonamide as a solid (yield 77%).

$^1$H NMR (400 MHz, CDCl$_3$): δ 3.08 (3H, s), 3.38 (3H, s), 7.30 (1H, d, J=4.4 Hz), 7.71 (1H, d, J=8.4 Hz), 8.04 (1H, dd, J=2 and 8.4 Hz), 8.14 (1H, d, J=2.4 Hz), 8.83 (1H, s), 8.99 (1H, d, J=4.4 Hz).

MS (ES) m/z=382 (MH$^+$)
HPLC=98.5%

PREPARATIVE EXAMPLE 8

N-{2-chloro-5-[3-cyano-pyrazolo[1,5-a]pyrimidin-7-yl]-phenyl}-N-methyl-methanesulfonamide A mixture of 0.042 g (0.39 mmol) of 5-amino-1H-pyrazole-4-carbonitrile and 0.124 g (0.39 mmol) of N-[5-(3-dimethylamino-acryloyl)-2-chloro-phenyl]-N-methyl-methanesulfonamide in 12 mL of glacial acetic acid was refluxed for 1.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 99 mg of N-{2-chloro-5-[3-cyano-pyrazolo[1,5-a]pyrimidin-7-yl]-phenyl}-N-methyl-methanesulfonamide as a solid (yield 70%).

$^1$H NMR (400 MHz, CDCl$_3$): δ 3.08 (3H, s), 3.37 (3H, s), 7.20 (1H, d, J=4.4 Hz), 7.69 (1H, d, J=8.8 Hz), 8.05 (1H, dd, J=2.4 and 8.8 Hz), 8.16 (1H, d, J=1.6 Hz), 8.42 (1H, s), 8.78 (1H, d, J=4.4 Hz).

MS (ES) m/z=362 (MH$^+$)

HPLC=93.7%

PREPARATIVE EXAMPLE 9

N-{2-fluoro-5-[3-cyano-2-methyl-pyrazolo[1,5-a]pyrimidin-7-yl]-phenyl}-N-methyl-acetamide A mixture of 0.046 g (0.38 mmol) of 5-amino-3-methyl-1H-pyrazole-4-carbonitrile and 0.1 g (0.38 mmol) of N-[5-(3-dimethylamino-acryloyl)-2-fluoro-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 92 mg of N-{2-fluoro-5-[3-cyano-2-methyl-pyrazolo[1,5-a]pyrimidin-7-yl]-phenyl}-N-methyl-acetamide as a solid (yield 75%).

$^1$H NMR (400 MHz, CDCl$_3$): δ 1.98 (3H, s), 2.61 (3H, s), 3.3 (3H, s), 7.09 (1H, d, J=4 Hz), 7.39-7.44 (1H, m), 7.89-8.02 (1H, m), 8.08-8.11 (1H, m), 8.70 (1H, d, J=4.4 Hz).

MS (ES) m/z=324 (MH$^+$)

HPLC=98.4%

PREPARATIVE EXAMPLE 10

N-{2-chloro-5-[3-cyano-2-methyl-pyrazolo[1,5-a]pyrimidin-7-yl]-phenyl}-N-methyl-acetamide A mixture of 0.055 g (0.43 mmol) of 5-amino-3-methyl-1H-pyrazole-4-carbonitrile and 0.120 g (0.43 mmol) of N-[5-(3-dimethylamino-acryloyl)-2-chloro-phenyl]-N-methyl-acetamide in 12 mL of glacial acetic acid was refluxed for 1.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 106 mg of N-{2-chloro-5-[3-cyano-2-methyl-pyrazolo[1,5-a]pyrimidin-7-yl]-phenyl}-N-methyl-acetamide as a solid (yield 73%).

$^1$H NMR (400 MHz, CDCl$_3$): δ 1.91 (3H, s), 2.61 (1H, s), 3.25 (3H, s), 7.10 (1H, d, J=4.8 Hz), 7.73 (1H, d, J=8.4 Hz), 7.97 (1H, dd, J=2 and J=8 Hz), 8.08 (1H, d, J=2.4 Hz), 8.71 (1H, d, J=4.4 Hz).

MS (ES) m/z=340 (MH$^+$)

HPLC=99.6%

PREPARATIVE EXAMPLE 11

N-{2-fluoro-5-[3-cyano-2-methyl-pyrazolo[1,5-a]pyrimidin-7-yl]-phenyl}-N-methyl-methanesulfonamide A mixture of 0.041 g (0.33 mmol) of 5-amino-3-methyl-1H-pyrazole-4-carbonitrile and 0.1 g (0.33 mmol) of N-[5-(3-dimethylamino-acryloyl)-2-fluoro-phenyl]-N-methyl-methanesulfonamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 66 mg of N-{2-fluoro-5-[3-cyano-2-methyl-pyrazolo[1,5-a]pyrimidin-7-yl]-phenyl}-N-methyl-methanesulfonamide as a solid (yield 55%).

$^1$H NMR (400 MHz, CDCl$_3$): δ 2.78 (3H, s), 3.17 (3H, s), 3.54 (3H, s), 7.24 (1H, d, J=4.4 Hz), 7.51-7.56 (1H, m), 8.25-8.31 (2H, m), 8.84 (1H, d, J=4.4 Hz).

MS (ES) m/z=360 (MH$^+$)

HPLC=98.9%

PREPARATIVE EXAMPLE 12

N-{2-chloro-5-[3-cyano-2-methyl-pyrazolo[1,5-a]pyrimidin-7-yl]-phenyl}-N-methyl-methanesulfonamide A mixture of 0.048 g (0.39 mmol) of 5-amino-3-methyl-1H-pyrazole-4-carbonitrile and 0.124 g (0.39 mmol) of N-[5-(3-dimethylamino-acryloyl)-2-chloro-phenyl]-N-methyl-methanesulfonamide in 12 mL of glacial acetic acid was refluxed for 1.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 89 mg of N-{2-chloro-5-[3-cyano-2-methyl-pyrazolo[1,5-a]pyrimidin-7-yl]-phenyl}-N-methyl-methanesulfonamide as a solid (yield 60.5%).

$^1$H NMR (400 MHz, CDCl$_3$): δ 2.61 (3H, s), 3.08 (1H, s), 3.66 (3H, s), 7.10 (1H, d, J=4.8 Hz), 7.68 (1H, d, J=8.8 Hz), 8.04 (1H, dd, J=2.4 and J=8.8 Hz), 8.15 (1H, d, J=2.4 Hz), 8.70 (1H, d, J=4.4 Hz).

MS (ES) m/z=376 (MH$^+$)

HPLC=98.1%

PREPARATIVE EXAMPLE 13

N-{2-methyl-5-[3-(thiophene-2-carbonyl)-pyrazolo[1,5-a]pyrimidin-7-yl]-phenyl}-N-methyl-acetamide A mixture of 0.074 g (0.38 mmol) of (5-amino-1H-pyrazol-4-yl)-thiophene-2-yl-methanone and 0.1 g (0.38 mmol) of N-[5-(3-dimethylamino-acryloyl)-2-methyl-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 132 mg of N-{2-methyl-5-[3-(thiophene-2-carbonyl)-pyrazolo[1,5-a]pyrimidin-7-yl]-phenyl}-N-methyl-acetamide as a solid (yield 88%).

$^1$H NMR (400 MHz, CDCl$_3$): δ 1.87 (3H, s), 2.37 (3H, s), 3.25 (3H, s), 7.13 (1H, d, J=4 Hz), 7.18-7.20 (1H, m), 7.54 (1H, D, J=7.6 Hz), 7.70 (1H, d, J=5.2 Hz), 7.94-7.98 (2H, m), 8.08 (1H, d, J=2.8 Hz), 8.71 (1H, s), 8.81 (1H, d, J=4 Hz).

MS (ES) m/z=391 (MH$^+$)
HPLC=98.3%

PREPARATIVE EXAMPLE 14

N-{2-methoxy-5-[3-(thiophene-2-carbonyl)-pyrazolo[1,5-a]pyrimidin-7-yl]-phenyl}-N-methyl-acetamide A mixture of 0.070 g (0.36 mmol) of (5-amino-1H-pyrazol-4-yl)-thiophene-2-yl-methanone and 0.1 g (0.38 mmol) of N-[5-(3-dimethylamino-acryloyl)-2-methoxy-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 135 mg of N-{2-methoxy-5-[3-(thiophene-2-carbonyl)-pyrazolo[1,5-a]pyrimidin-7-yl]-phenyl}-N-methyl-acetamide as a solid (yield 92%).

$^1$H NMR (400 MHz, CDCl$_3$): δ 1.90 (3H, s), 3.23 (3H, s), 3.97 (3H, s), 7.12 (1H, d, J=4.8 Hz), 7.17-7.21 (2H, m), 7.70 (1H, d, J=4.4 Hz), 8.02 (1H, S), 8.09 (1H, d, J=4 Hz), 8.15 (1H, d, J=8.8 Hz), 8.71 (1H, s), 8.79 (1H, d, J=4.4 Hz).

MS (ES) m/z=407 (MH$^+$)
HPLC=100%

PREPARATIVE EXAMPLE 15

N-{2,4-difluoro-5-[3-(thiophene-2-carbonyl)-pyrazolo[1,5-a]pyrimidin-7-yl]-phenyl}-N-methyl-acetamide A mixture of 0.217 g (1.12 mmol) of (5-amino-1H-pyrazol-4-yl)-thiophene-2-yl-methanone and 0.3 g (1.12 mmol) of N-[5-(3-dimethylamino-acryloyl)-2,4-difluoro-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 320 mg of N-{2,4-difluoro-5-[3-(thiophene-2-carbonyl)-pyrazolo[1,5-a]pyrimidin-7-yl]-phenyl}-N-methyl-acetamide as a solid (yield 69%).

$^1$H NMR (250 MHz, CDCl$_3$): δ 1.82 (3H, s), 3.11 (3H, s), 6.96-7.06 (3H, m), 7.55 (1H, d, J=4.9 Hz), 7.76 (1H, t, J=8.2 Hz), 7.91 (1H, dd, J=1 and 3.6 Hz), 8.52 (1H, s), 8.68 (1H, d, J=4.1 Hz).

MS (ES) m/z=413 (MH$^+$)
HPLC=99.0%

PREPARATIVE EXAMPLE 16

N-{5-fluoro-2-methoxy-3-[3-(thiophene-2-carbonyl)-pyrazolo[1,5-a]pyrimidin-7-yl]-phenyl}-N-methyl-acetamide A mixture of 0.180 g (0.93 mmol) of (5-amino-1H-pyrazol-4-yl)-thiophene-2-yl-methanone and 0.275 g (0.93 mmol) of N-[3-(3-dimethylamino-acryloyl)-5-fluoro-2-methoxy-phenyl]-N-methyl-acetamide in 10 mL of glacial acetic acid was refluxed for 2.5 hours and then the solvent was removed by reduced pressure distillation. To the resulting residue were added 15 mL of dichloromethane and 10 mL of saturated sodium bicarbonate solution. The two layers were separated, and the aqueous layer was washed with 10 mL of dichloromethane. The organic layers were washed with 10 mL of water and dried over magnesium sulfate. The dichloromethane layer was evaporated to dryness to yield an oil which, in the presence of ethyl acetate, gave 160 mg of N-{5-fluoro-2-methoxy-3-[3-(thiophene-2-carbonyl)-pyrazolo[1,5-a]pyrimidin-7-yl]-phenyl}-N-methyl-acetamide as a solid (yield 40%).

$^1$H NMR (250 MHz, CDCl$_3$): δ 2.04 (3H, s), 3.32 (3H, s), 3.56 (3H, s), 7.09-7.25 (3H, m), 7.35 (1H, dd, J=2.2 and J=7.1 Hz), 7.72 (1H, d, J=4.9 Hz), 8.12 (1H, d, J=3.8 Hz), 8.68 (1H, s), 8.85 (1H, d, J=4 Hz).

MS (ES) m/z=425 (MH$^+$)
HPLC=98.4%

COMPOSITION EXAMPLE 1

5 mg Tablets

| | |
|---|---|
| Active ingredient | 5.0 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

COMPOSITION EXAMPLE 2

10 mg Capsules

| | |
|---|---|
| Active ingredient | 10.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline cellulose q.s. to | 155.0 mg |

COMPOSITION EXAMPLE 3

Oral Drops

| | |
|---|---|
| Active ingredient | 0.5 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified water q.s. to | 100.0 mL |

COMPOSITION EXAMPLE 4

2.5 mg Tablets

| | |
|---|---|
| Active ingredient | 2.5 mg |
| Colloidal silicon dioxide | 0.6 mg |
| Croscarmellose sodium | 12.0 mg |
| Talc | 4.0 mg |
| Magnesium stearate | 1.5 mg |
| Polysorbate 80 | 1.0 mg |
| Lactose | 75.0 mg |
| Hydroxypropyl methylcellulose | 3.0 mg |
| Polyethylene glycol 4000 | 0.5 mg |
| Titanium dioxide E171 | 1.5 mg |
| Microcrystalline cellulose q.s. to | 125.0 mg |

COMPOSITION EXAMPLE 5

5 mg Capsules

| | |
|---|---|
| Active ingredient | 5.0 mg |
| Colloidal silicon dioxide | 0.6 mg |
| Crospovidone | 12.0 mg |
| Talc | 4.0 mg |
| Magnesium stearate | 1.5 mg |
| Lauryl sulfate sodium | 1.5 mg |
| Lactose | 77.0 mg |
| Gelatin | 28.5 mg |
| Titanium dioxide E171 | 1.5 mg |
| Indigotin E132 | 0.02 mg |
| Microcrystalline q.s. to | 155.0 mg |

COMPOSITION EXAMPLE 6

Oral Drops

| | |
|---|---|
| Active ingredient | 0.25 g |
| Propylene glycol | 10.0 g |
| Glycerin | 5.0 g |
| Saccharin sodium | 0.1 g |
| Polysorbate 80 | 1.0 g |
| Lemon flavor | 0.2 g |
| Ethanol | 25.0 mL |
| Purified q.s. to | 100.0 mL |

The invention claimed is:

1. A compound selected from the group consisting of:
   a) N-{2-fluoro-5-[3-nitro-pyrazolo[1,5-a]pyrimidin-7-yl]-phenyl}-N-methyl-acetamide;
   b) N-{2-fluoro-5-[3-cyano-pyrazolo[1,5-a]pyrimidin-7-yl]-phenyl}-N-methyl-acetamide;
   c) N-{2-chloro-5-[3-nitro-pyrazolo[1,5-a]pyrimidin-7-yl]-phenyl}-N-methyl-acetamide;
   d) N-{2-chloro-5-[3-cyano-pyrazolo[1,5-a]pyrimidin-7-yl]-phenyl}-N-methyl-acetamide;
   e) N-{2-fluoro-5-[3-nitro-pyrazolo[1,5-a]pyrimidin-7-yl]-phenyl}-N-methyl-methanesulfonamide;
   f) N-{2-fluoro-5-[3-cyano-pyrazolo[1,5-a]pyrimidin-7-yl]-phenyl}-N-methyl-methanesulfonamide;
   g) N-{2-chloro-5-[3-nitro-pyrazolo[1,5-a]pyrimidin-7-yl]-phenyl}-N-methyl-methanesulfonamide;
   h) N-{2-chloro-5-[3-cyano-pyrazolo[1,5-a]pyrimidin-7-yl]-phenyl}-N-methyl-methanesulfonamide;
   i) N-{2-fluoro-5-[3-cyano-2-methyl-pyrazolo[1,5-a]pyrimidin-7-yl]-phenyl}-N-methyl-acetamide;
   j) N-{2-chloro-5-[3-cyano-2-methyl-pyrazolo[1,5-a]pyrimidin-7-yl]-phenyl}-N-methyl-acetamide;
   k) N-{2-fluoro-5-[3-cyano-2-methyl-pyrazolo[1,5-a]pyrimidin-7-yl]-phenyl}-N-methyl-methanesulfonamide;
   l) N-{2-chloro-5-[3-cyano-2-methyl-pyrazolo[1,5-a]pyrimidin-7-yl]-phenyl}-N-methyl-methanesulfonamide;
   m) N-{2-methyl-5-[3-(thiophene-2-carbonyl)-pyrazolo[1,5-a]pyrimidin-7-yl]-phenyl}-N-methyl-acetamide;
   n) N-{2-methoxy-5-[3-(thiophene-2-carbonyl)-pyrazolo[1,5-a]pyrimidin-7-yl]-phenyl}-N-methyl-acetamide;
   o) N-{2,4-difluoro-5-[3-(thiophene-2-carbonyl)-pyrazolo[1,5-a]pyrimidin-7-yl]-phenyl}-N-methyl-acetamide; and
   p) N-{5-fluoro-2-methoxy-3-[3-(thiophene-2-carbonyl)-pyrazolo[1,5-a]pyrimidin-7-yl]-phenyl}-N-methyl-acetamide;
   or pharmaceutically acceptable salts thereof.

2. A compound of claim 1 selected from the group consisting of:
   f) N-{2-fluoro-5-[3-cyano-pyrazolo[1,5-a]pyrimidin-7-yl]-phenyl}-N-methyl-methanesulfonamide;
   h) N-{2-chloro-5-[3-cyano-pyrazolo[1,5-a]pyrimidin-7-yl]-phenyl}-N-methyl-methanesulfonamide;
   k) N-{2-fluoro-5-[3-cyano-2-methyl-pyrazolo[1,5-a]pyrimidin-7-yl]-phenyl}-N-methyl-methanesulfonamide; and l) N-{2-chloro-5-[3-cyano-2-methyl-pyrazolo[1,5-a]pyrimidin-7-yl]-phenyl}-N-methyl-methanesulfonamide;

or pharmaceutically acceptable salts thereof.

3. A method for treating anxiety in a human or non-human mammal in need thereof, the method comprising administration to said human or non-human mammal a therapeutically effective amount of the compound of claim 1 or a pharmaceutically acceptable salt thereof.

4. A method for treating epilepsy in a human or non-human mammal in need thereof, the method comprising administration to said human or non-human mammal a therapeutically effective amount of the compound of claim 1 or a pharmaceutically acceptable salt thereof.

5. A method for treating sleep disorders in a human or non-human mammal in need thereof, the method comprising administration to said human or non-human mammal a therapeutically effective amount of the compound of claim 1 or a pharmaceutically acceptable salt thereof.

6. A method for treating insomnia in a human or non-human mammal in need thereof, the method comprising administration to said human or non-human mammal a therapeutically effective amount of the compound of claim 1 or a pharmaceutically acceptable salt thereof.

7. A method for inducing sedation-hypnosis in a human or non-human mammal in need thereof, the method comprising administration to said human or non-human mammal a therapeutically effective amount of the compound of claim 1 or a pharmaceutically acceptable salt thereof.

8. A method for inducing anesthesia in a human or non-human mammal in need thereof, the method comprising administration to said human or non-human mammal a therapeutically effective amount of the compound of claim 1 or a pharmaceutically acceptable salt thereof.

9. A method for modulating the necessary time to induce sleep and its duration in a human or non-human mammal in need thereof, the method comprising administration to said human or non-human mammal a therapeutically effective amount of the compound of claim 1 or a pharmaceutically acceptable salt thereof.

10. A method for inducing muscle relaxation in a human or non-human mammal in need thereof, the method comprising administration to said human or non-human mammal a therapeutically effective amount of the compound of claim 1 or a pharmaceutically acceptable salt thereof.

11. A pharmaceutical composition comprising a therapeutically effective amount of a compound as defined in claim 1, together with an appropriate amount of at least one pharmaceutical excipient or carrier.

* * * * *